United States Patent
Menichelli et al.

(10) Patent No.: US 10,702,717 B2
(45) Date of Patent: Jul. 7, 2020

(54) ONE DIMENSIONAL TRANSMISSION DETECTOR FOR RADIOTHERAPY

(71) Applicant: Ion Beam Applications S.A., Louvain-la-Neuve (BE)

(72) Inventors: David Menichelli, Louvain-la-Neuve (BE); Lutz Müller, Louvain-la-Neuve (BE); Jochen Krimmer, Louvain-la-Neuve (BE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 100 days.

(21) Appl. No.: 16/136,374

(22) Filed: Sep. 20, 2018

(65) Prior Publication Data

US 2019/0083816 A1    Mar. 21, 2019

Related U.S. Application Data

(60) Provisional application No. 62/561,152, filed on Sep. 20, 2017.

(51) Int. Cl.
*A61N 5/10* (2006.01)
*G01T 1/29* (2006.01)

(52) U.S. Cl.
CPC ......... *A61N 5/1075* (2013.01); *A61N 5/1045* (2013.01); *A61N 5/1071* (2013.01); *A61N 5/1081* (2013.01); *G01T 1/2935* (2013.01); *A61N 2005/1087* (2013.01)

(58) Field of Classification Search
None
See application file for complete search history.

(56) References Cited

U.S. PATENT DOCUMENTS

| | | | | |
|---|---|---|---|---|
| 8,218,725 B2* | 7/2012 | Muller | ................ | A61N 5/1048 250/252.1 |
| 9,199,093 B2* | 12/2015 | Brusasco | ............ | A61N 5/1048 |
| 2008/0170663 A1* | 7/2008 | Urano | ................. | A61N 5/1042 378/65 |

(Continued)

*Primary Examiner* — Andrew Smyth
(74) *Attorney, Agent, or Firm* — Finnegan, Henderson, Farabow, Garrett & Dunner LLP (57) ABSTRACT

A sensing device for a radiation therapy apparatus, the apparatus comprising an accelerator and a beam-shaping device the beam shaping device being a multi-leaf collimator (MLC) (2) having a plurality of pairs of leaves, and a rotatable gantry, the sensing device comprising:
  a transmission electronic detector (1) comprising an array of ionization chambers. The ionization chambers are defined by a bias electrode (11a,11b, 34,42) on the one hand and by a planar array of conductive strips (40) or strip assemblies (30) on the other hand. The strips or strip assemblies are associated to the leaf pairs of the MLC. The strips are the collecting electrodes of the ionization chambers. Each strip assembly or in the case of one particular embodiment, each strip, yields two currents which allow to determine the position of the leaves of a leaf pair associated with the strip or strip assembly,
  a gantry sensor configured to determine at least one position associated with a gantry angle; and
  a processor, adapted to determine the position of at least one pair of leaves of the MLC using the currents $i_1$ and $i_2$ obtained from the collecting electrode strips.

15 Claims, 4 Drawing Sheets

(56) References Cited

U.S. PATENT DOCUMENTS

2010/0177872 A1* 7/2010 Muller ................. A61N 5/1048
378/65
2012/0232324 A1* 9/2012 Brusasco ............. A61N 5/1042
600/1

* cited by examiner

ONE DIMENSIONAL TRANSMISSION DETECTOR FOR RADIOTHERAPY

CROSS-REFERENCE TO RELATED PATENT APPLICATIONS

This application claims the benefit of U.S. Provisional Application No. 62/561,152, filed Sep. 20, 2017, which is hereby incorporated by reference in its entirety.

TECHNICAL FIELD

The present invention relates to radiation therapy equipment, and in particular, to devices adapted for enabling quality assurance of external beam radiation therapy for devices using a multi-leaf collimator.

BACKGROUND OF THE INVENTION

Minimizing the harm to organs at risk, while maximizing the effectiveness of treatment, requires precise determination of actual dose delivered and a comparison to the treatment plan.

This treatment plan, prepared following the prescription of the radiation oncologist, requires precise, accurate, and consistent delivery of an optimal radiation dose to the tumor while simultaneously reducing the side effects on healthy surrounding tissues.

At present, state-of-the art radiation therapy includes using a multi-leaf collimator to modulate the intensity of the radiation beam produced by a particle beam accelerator, such as a LINAC (conventional radiation-emitting, linear accelerator), to better shape the radiation dose distribution in order to minimize irradiation of non-tumorous cells. A multi-leaf collimator (MLC) is a device made up of individual "leaves" of metal, typically high atomic-number materials such as tungsten. The leaves move independently in and out of the beam aperture in order to partially block the beam. MLCs typically include two banks of opposing leaves. In typical examples, each bank has from approximately 50 to 200 leaves, each leaf having a width in the range from about 0.25 cm to about 2 cm (projected at isocenter). A given leaf in a bank and the opposite one in the other bank form a "leaf pair"; they can move one against the other (thus obstructing the beam) or apart (creating an aperture which, in most installations, can be also asymmetric with respect to the central beam axis [leaf overtravel]). Accordingly, today's treatment plans rely on a properly functioning MLC for Intensity Modulated Radiation Therapy (IMRT). Ideally, verification, in real time, that the MLC is properly operating would allow adaptions to subsequent treatment plans or even an adaptation during delivery The delivered dose may vary from the intended (planned) treatment dose due to a number of factors. These factors include the wrong treatment planning system (TPS) calculation, an error or fault in the physical movement of the LINAC, including its collimating system, or an incorrect beam energy of the LINAC, errors in patient positioning, or changes in the patient's anatomy.

Risks of errors is particularly high in the case of plans with high modulation (i.e. a highly conformal dose distribution is obtained with a complex dynamics of the MLC, in such a way that many small beams contribute to the overall dose).

The effect of errors on patient's health is then amplified in the case of stereotactic treatments, in which the overall treatment dose is delivered in one or a few fractions (i.e. treatment sessions) instead of using the more traditional approach of many fractions (e.g. 20-30) delivered in subsequent days. Stereotactic treatments are appealing since they increase workflow efficiency, reduce problems related to inter-fractional anatomy changes and, in some cases, present a radiobiological advantage. However, delivering a wrong dose may have severe and irreparable consequences.

In traditional pre-treatment quality assurance (QA), a phantom-based detector rests on the couch (replacing the patient) and is irradiated with the treatment plan. This test reveals calculation errors and systematic LINAC errors, and sometimes resulting dose distributions are projected into the patient anatomy with the assumption that it conforms to the CT scan taken at the time of planning. However, this test is not effective against lack of LINAC repeatability, positioning errors, and anatomical changes, as it is done in a special QA fraction and not during patient treatment. Additionally, such pre-treatment QA adds an additional step in the clinical workflow, reducing its efficiency.

Radiation sensors suited to quality assurance categorize as either passive or active sensors. Passive sensors cannot alone produce a signal, thus they need to be coupled to a readout system after irradiation. Examples of passive sensors include radiographic and radiochromic films, gels, sensors based on optically- or thermally stimulated luminescence. Active sensors, permanently connected to an electronic readout system, immediately provide a readout signal during irradiation. Examples of active sensors include semiconductor diodes or ion chambers. Active sensors are preferable since they are easier and faster to use, thus increasing the efficiency of the radiotherapy workflow. Moreover, these detectors allow the instantaneous signal readout (not only integrated signal) and are suited to track dynamical changes.

Well known examples of active sensors for radiotherapy include diodes and ionization chambers. U.S. Pat. No. 6,125,335 describes an example of a diode detector having a beam profiler which is in the form of an array of 46 sensor diodes and an off-axis horizontal sensor diode array. Another example of a typical beam profiler is a multi-sensor radiation detector array, such as the Profiler Model 1170 by Sun Nuclear Corporation of Melbourne, Fla., USA.

Active sensors, typically organized in an array, provide the spatial resolution necessary to verify the complex radiation patterns generated by an MLC. Known ionization chamber arrays include a device described by Bonin et al., "A pixel chamber to monitor the beam performances in hadron therapy" published in *Nuclear Instruments and Methods in Physics Research*, No. A 519 (2004) at pages 674-686. This device includes a 2-D array of 1024 successive ionization chambers arranged in a regular matrix of 32×32 pixels.

Ionization chambers generally work by providing a high-voltage difference between two electrodes. A gas or liquid fills the space between the electrodes. Typically, this gas is air, nitrogen or an organic gas. Alternatively, an electrically insulating liquid fills this space. The medium gets ionized when exposed to radiation. The ions move towards the electrodes and their charge is collected. An external electrometer measures this charge. The ionization of a molecule of the medium requires a known average energy and, depending on the gas and on the irradiation type, the collected charge is directly proportional to the energy deposited in the gas.

U.S. Pat. No. 4,988,866 describes yet another dosimetry device having a limited number of specifically located sensors for measuring. This device has at least two significant shortcomings. First, due to its configuration and limited number of sensors, it cannot verify the structure of a radiation field of any size. Second, the device can only measure a very narrow energy range due to the single absorber.

Still another dosimetry device, described in DE-101 43 609, improves the spatial resolution of measurement without increasing the number of individual sensors. A set of sensors arranged in a first line and positioned on a rotatable support are located at a different radius from a second line of sensors. The support successively rotates along an angle of 1° or 2°. Successive measurements by lines of sensors taken at angular steps result in a set of many measurement points, thus giving higher spatial resolution. However, this device requires a mechanical drive for the sensor, and the measurement is more time-consuming. In addition, because one takes a set of measurements at successive times, one relies on the stability and constancy of the radiation source. This device cannot measure radiation beam energy.

Although some of the devices of the state of the art measure energy using build-up plates of different thicknesses, the user must enter into the treatment room to perform the measurement several times with the required build-up plate for different energies.

Yang, Y. and Xing, L. describe a method for determining the position of a leaf of a MLC in "*Using the volumetric effect of a finite-sized detector for routine quality assurance of multi leaf collimator leaf positioning*" Med. Phys. 30 (2003) 433-441. They disclose a finite-size detector, such as an ion chamber, positioned on one leaf as projected in the isocenter plane. Leaf-position displacement increases or decreases the irradiated volume of the detector; therefore, measurement of dose relates to a leaf position error.

Islam et al., in U.S. Pat. No. 8,119,978, issued 2012 Feb. 21, describes an area integrating fluence-monitoring sensor for measuring radiation dose. The sensor consists of at least one gradient ion chamber having a volume gradient across its length.

To detect LINAC errors, which may not be present during first plan delivery, and to increase the efficiency of the clinical workflow, the QA measurement repeats for each treatment fraction while the patient lies on the couch (in-vivo QA). One important benefit is that in-vivo QA enables treatment interruption if something starts to go wrong.

Early attempts for in-vivo QA taught taping a few point detectors (usually diodes) to the patient's skin. This verification, however, was limited to few points and measurement uncertainty was high (conversion from the dose measured at skin level and the one in the target depends on many parameters). In addition, these detectors introduced a perturbation to dose distribution. This method requires positioning of the probes in areas of flat dosimetric gradients, which is usually not given for Intensity Modulated Treatments.

More recent known devices incorporate either entrance (transmission) or exit (portal) detectors.

Other known devices allow the user to evaluate the beam fluence, and thus to project results into the patient's anatomy. Fluence detectors estimate dose perturbation based on detected errors and modify the revealed dose distribution inside the patient accordingly using a dose engine combined with the patient's CT images. Updated images of the patient (e.g. taken with CBCT) in lieu of the planning CT scan can account for positioning errors and any anatomical changes.

Various solutions are known for verifying in vivo the dose distribution in a patient. A first solution uses transmission detectors. The detector positions between the LINAC's collimating system and the patient. The collection of measured data (not perturbed by the patient and the couch) is accomplished by sensors with high-dosimetric performance, such as ion chambers.

Müller in U.S. Pat. No. 8,160,204 issued 2012 Apr. 17, for example, teaches the determination of photon and electron fluence distributions based on measurements. Comparing the expected detector response (calculated from the patient plan on a detector model) to measured data enables a calculation of the difference between actually delivered fluence and the planned fluence.

One particularly well suited detector includes the MatriXX brand detector paired with the COMPASS 3D brand software tool, both available from IBA Dosimetry GmbH (Bahnhofstrasse 5, 90592 Schwarzenbruck, Germany). This is a system for 3D treatment plan and delivery verification and patient dose analysis, giving clinically relevant data analysis. The software component of this detector reconstructs dose from measured fluence, compares the patient plan with measurements, and provides 3D dose deposition information inside the patient's anatomy. Accordingly, this arrangement enables visual or statistical plan evaluation (evaluating dose differences/gamma relative to TPS inside patient CT or on a structure-by-structure statistical/quantitative basis via comparison of the TPS generated DVHs to that of this device's independently calculated DVHs).

Drawbacks of these known detectors include perturbation of the beam under measurement, reduced space between the patient's head and the couch, and loss of the option of mounting additional accessories at the LINAC. Additionally, radiation scattered from the LINAC's head and collimator, which does not contribute to the dose in the patient, complicates the beam measurement, and modeling with available dose engines and predicting the response becomes difficult.

A second solution, a system based on portal imagers, offers a practical solution because most LINAC devices are equipped with a system for portal imaging (typically an amorphous-silicon flat-panel with high spatial resolution) dedicated to control patient positioning. In this example, the QA system consists simply of an additional software. Although there are many commercial solutions available, only few are suited to evaluate the fluence, and calculate the dose in the patient's anatomy. Examples of such commercial systems include EPlgray (available from DOSIsoft, SA, 47 Avenue Carnot, 94230 Cachon, France), and PerFraction (available from Sun Nuclear Corp., 3275 Suntree Blvd, Melbourne, Fla. 32940). All these solutions suffer of similar limitations including: Portal imagers are optimized for patient imaging and positioning—not dosimetry—and thus require complex dosimetric calibration. Fluence has to be back-projected through the patient, increasing uncertainty; and the intensive QA use may cause radiation damage to the detector. Moreover, they usually cover only a part of the maximum field opening and are therefore not suited for all treatments.

A third solution to determine the fluence uses protocol files, such as LINAC log files generated during delivery, to calculate dose values and distributions received by the patient. Commercial products using log files in this way include Mobius 3D with FX extension (Mobius medical). Persons having ordinary skill in this art debate whether log files can provide the same degree of QA reliability as measurements, as they are generated by the system to be monitored itself. Options of suitable transmission detectors include a two-dimensional (2D) array with parallel readout (i.e., each pixel connects to an individual channel of the readout electronics). This enables a true measurement of the 2D fluence distribution. A main limitation of such a 2D detector includes that complexity (e.g. the number of readout channels) increases as spatial resolution is increased. For instance, for a square detector of side length L segmented with a uniform distribution of pixels with pitch h—the number of readout channels is $(L/h)^2$. It is thus difficult to reach a resolution suitable to verify stereotactic treatments, characterized by steep dose gradients. However, two commercial solutions are available: A first commercial solution is the DOLPHIN-branded dosimetry detector, available from IBA Dosimetry GmbH (Bahnhofstrasse 5, 90592 Schwarzenbruck, Germany). It measures the dose using a 2D ion-chamber pixel array (about 1600 pixels with 5 mm pixel pitch projected to isocenter. The Dolphin-brand detector, however, has limitations. For example, alignment of pixels' rows with MLC leaf pairs is not possible since pixel pitch is larger than typical leaves width. Also, due to constraints of pixel ion-chamber design, the Dolphin-brand detector is limited in terms of attenuation, spatial resolution and patient clearance.

A second commercial solution, the ScandiDos Delta4 Discovery brand (available from Scandidos AB, SE-751 83 Uppsala, Sweden) is based on a 2D transmission detector similar to Dolphin brand detector (available from IBA Dosimetry GmbH (Bahnhofstrasse 5, 90592 Schwarzenbruck, Germany). However the ScandiDos device uses a larger number (about 4000) of smaller sensors (silicon diodes), which are aligned with MLC leaf pairs. For online use, it requires a pre-treatment measurement with a phantom-based array to correlate transmission array measurements and dose.

Two-dimensional (2D) arrays with multiplexed readout using large area solid-state technology associates a set of pixels (e.g. a column) to the same readout channel. Complexity increases linearly in relation to the reduction in pixel pitch. However, the cost of solid-state sensors increase more than linearly with area (one pays for the full area, not only the portion covered by pixels). To date there are no commercial applications, although use of MAPS (monolithic active pixel sensors) has been investigated at research level.

An integral ion chamber, covering the full beam area, can be used for QA purposes too (see, e.g., Islam U.S. Pat. No. 8,119,978). A commercial implementation is the detector IQM (from iRT Systems GmbH, Koblenz, Germany). Since a large parallel plate ion chamber would be suitable to track the integrated fluence only, one of the electrodes is inclined in order to introduce sensitivity to rigid displacements of the MLC aperture, as anticipated by the teaching of Barthelmes (U.S. Pat. No. 4,803,368). The IQM is actually composed of two integral chambers mounted back to back, in order to increase the overall detector sensitivity to errors. According to Islam (WO2016191883) the collecting electrode of the integral chamber can be segmented into two interdigitated electrodes with separate readout, in order to obtain with a parallel plate configuration the same error sensitivity which would be given by an inclined electrode, thus simplifying the construction of the device.

One-dimensional (1D) arrays of linear sensors can deliver a complete measurement the number of degrees of freedom of the two-dimensional (2D) fluence distribution generated by the one-dimensional motion of the collimator leaves. Thus, one sensor can monitor the motion of each leaf-pair. An early commercial example is provided by the DAVID system (PTW Freiburg, Germany), based on an array of wire ion chambers (one wire is associated to each leaf pair). Measurements taken with this detector during a given fraction are compared with a baseline measured during or before the first fraction (which is assumed to be in agreement with the plan), in order to perform a constancy check.

With a more complex arrangement, 1D linear detectors can do more than performing a constancy check or measuring the integrated fluence. In particular, it is possible to determine the position of a pair of leaves and not the true dose. One example is a one-dimensional (1D) scintillating fiber optic array developed by Beaulieu et al. (see for example U.S. Pat. No. 8,183,534, which describes a scintillating optical fiber placed below each leaf pair, and a readout at both extremities using two photodiodes. Fiber optic arrays, however, are difficult to calibrate, prone to radiation damage, and are less suited for beam monitoring.

If the 1D array measures the position of a leaf instead of a true dose, it can be relatively insensitive to electron contamination and can work with a minimal buildup. In this way, beam perturbation can be minimized. Such an 1D array detector can also estimate the flux (space integral of fluence), but not the true 2D fluence (e.g. one has to assume a given beam profile e.g. from TPS commissioning.

The above considerations yield the rationale for developing an improved detector for online measurement of radiation dose distribution during treatment, when the patient is in position on the couch.

SUMMARY OF THE INVENTION

The present invention provides an improvement with respect to the known art and solves limitations known in the art. The present invention includes a one-dimensional (1D) strip detector for measuring and determining radiation dose during treatment, when the patient is in position on the couch. The present invention further overcomes limitations of the current state-of-the-art. Specifically, the present invention provides a measurement system suitable to determine the fluence generated by a radiotherapy LINAC equipped with a MLC with an optimal balance between performance, cost and reliability.

According to a first aspect, the invention is related to a sensing device for a radiation therapy apparatus, the apparatus comprising an accelerator, a beam-shaping device, the beam shaping device being a multi-leaf collimator (MLC) (2) having a plurality of pairs of leaves, and a rotatable gantry, the sensing device comprising:

a transmission electronic detector comprising one or two bias electrodes and a planar 1D array of electrically conductive strip assemblies, and wherein:

each strip assembly comprises two strips which are oriented in the direction of the leaf pairs, and configured so that each leaf pair of the MLC is associated with one or more strip assemblies, when the detector is positioned between the MLC and a target of interest, each strip together with one of the bias electrodes defines an ion chamber, with the strip forming the collecting electrode thereof, the two strips of each assembly are configured to respectively produce two currents $i_1$ and $i_2$ when the detector is irradiated by a beam that is shaped by the MLC, and when an electric field is created between the bias electrode(s) and the strips, said currents allow to determine the position of the pair of MLC leaves associated with the strip assembly, for each strip assembly, a pair of electrometers comprising respective read-out amplifiers coupled respectively to the strips of the assembly, for measuring the currents $i_1$ and $i_2$, a gantry sensor configured to determine at least one position associated with a gantry angle; and a processor, adapted to determine the position of at least one pair of leaves of the MLC using the currents $i_1$ and $i_2$ obtained from the strip assemblies.

According to an embodiment of the first aspect of the invention, each strip assembly comprises two collecting electrodes mounted back to back, and wherein the detector comprises two planar bias electrodes which are conductive plates placed on either side of the planar 1D array of strip assemblies, and oriented in such a way that the distance between every strip on one side of the planar 1D array and the corresponding bias electrode increases monotonically along the length of the strip in a given direction along said length, while the distance between every strip on the other side and the corresponding bias electrode decreases monotonically along the length of the strip, in the same given direction. In the latter embodiment, the bias electrodes may be parallel to each other.

According to another embodiment of the first aspect of the invention each strip assembly comprises two adjacent collecting electrode strips, and wherein the width of the first electrode strip decreases monotonically along the length of the strip assembly in a given direction along said length, while the width of the second electrode strip increases monotonically in the same given direction, and wherein the detector further comprises one bias electrode in the form of a conductive plate that is parallel to the planar array of strip assemblies.

In the latter embodiment, the sensing device may further comprise a large area collecting electrode on the back side of the planar array of strip assemblies, and a second bias electrode parallel to the planar array of strip assemblies and facing said large area collecting electrode.

According a second aspect, the invention is related to a sensing device for a radiation therapy apparatus, the apparatus comprising an accelerator, a beam-shaping device the beam shaping device being a multi-leaf collimator (MLC) having a plurality of pairs of leaves, and a rotatable gantry, the sensing device comprising:

a transmission electronic detector comprising a bias electrode and a planar 1D array of electrically conductive strips oriented parallel to the bias electrode, and wherein:

each strip is oriented in the direction of the leaf pairs, and configured so that each leaf pair of the MLC is associated with one or more strips, when the detector is positioned between the MLC and a target of interest, each strip together with one of the bias electrodes defines an ion chamber, with the strip forming the collecting electrode thereof, each strip is configured to respectively produce two currents $i_1$ and $i_2$ at the opposite outer ends of the strip, when the detector is irradiated by a beam that is shaped by the MLC, and when an electric field is created between the bias electrode(s) and the strips, said currents allow to determine the position of the pair of MLC leaves associated with the strip assembly, for each strip, a pair of electrometers comprising respective read-out amplifiers coupled respectively to the opposite outer ends of the strip, for measuring the currents $i_1$ and $i_2$, a gantry sensor configured to determine at least one position associated with a gantry angle; and a processor, adapted to determine the position of at least one pair of leaves of the MLC using the currents $i_1$ and $i_2$ obtained from the strips.

A sensing device according to the second aspect may further comprise a large area collecting electrode on the back side of the planar array of strips, and a second bias electrode parallel to the planar array of strips and facing said large area collecting electrode.

According to further embodiments of the invention according to the first or second aspect:

the sensing device further comprises a receiver, configured to receive a patient plan (including patient dose, patient images taken before planning and radiation beam configuration); and the processor is adapted to compare expected (from plan) and measured LINAC behavior (in term of leaves position, flux and gantry angle).

The processor may further be configured to enable real-time signalling of a deviation from an expected behavior and a measured behavior exceeding a user-defined tolerance.

The sensing device may further comprise:

a storage means in communication with the processor, the storage means configured to store a beam model of the accelerator;

a fluence-reconstructing engine configured to compute a photon fluence based on the position of pairs of the leaves determined by the processor and on the beam model wherein the photon fluence is determined independently from a presence of a patient or phantom in the beam; and a dose calculation engine configured to compute a delivered 3D dose distribution using fluence and patient images.

The processor may further be adapted to compare a calculated delivered dose to a planned dose. The processor may further be configured to extract at least one subset of a 3D dose distribution and a set of quality parameters from the calculated 3D dose distribution.

The sensing device may further comprise:

an image acquisition station configured to acquire updated patient images;

an image processor configured to communicate the images to the dose calculation engine whereby the dose calculation engine calculates a dose distribution based on measured fluence and the updated patient images.

The processor may further be adapted to accumulate a plurality of data measurements relating to a corresponding plurality of dose delivered to the patient during consecutive fractions.

A further summary of characteristic features of the invention is given hereafter.

A. For a radiation therapy apparatus comprising a beam-shaping device comprising an accelerator, a multi-leaf collimator (MLC) and a rotatable gantry, a sensing device comprising:

(a) a transmission electronic detector comprising a 1D array comprising at least two ion chambers, whereby the transmission electronic detector disposes between the beam shaping device and a target of interest, wherein at least one ion chamber of the 1D array is associated with at least one pair of leaves of the MLC;

(b) a gantry sensor configured to determine at least one position associated with a first gantry angle; and (c) a processor, adapted to determine the position of the at least one pair of leaves of the MLC using data obtained from the at least two ion chambers of the 1D array.

B. The sensing device of paragraph A wherein:
(a) a receiver is configured to receive a patient plan (including patient dose, patient images taken before planning, and radiation beam configuration); and
(b) a processor adapted to compare expected (from plan) and measured LINAC behavior (in term of leaves position, flux and gantry angle).

The sensing device of paragraph B wherein:
the processor is further configured to enable real-time signaling a deviation from an expected behavior and a measured behavior exceeding a user-defined tolerance.

C. The sensing device of paragraph B, further comprising:
(a) a storage means in communication with the processor, the storage means configured to store a beam model of the accelerator;
(b) a fluence-reconstructing engine configured to compute a photon fluence based on the position of pairs of the leaves determined by the processor and on the beam model wherein the photon fluence is determined independently from a presence of a patient or phantom in the beam; and
(c) a dose calculation engine configured to compute a delivered 3D dose distribution using fluence and patient images.

D. The sensing device of paragraph C wherein:
the processor is further adapted to compare a calculated delivered dose to a planned dose.

E. The sensing device of paragraph C wherein:
the processor is further configured to extract at least one subset of a 3D dose distribution and a set of quality parameters from the calculated 3D dose distribution.

F. The sensing device of paragraph C further comprising:
a. an acquirer configured to acquire updated patient images;
b. an image processor configured to communicate the images to the dose engine whereby the dose engine calculates a dose distribution based on measured fluence and the updated patient images.

G. The sensing device according to paragraph C or paragraph F wherein:
the processor is further adapted to accumulate a plurality of data measurements relating to a corresponding plurality of dose delivered to the patient during consecutive fractions.

H. The sensing device according to any of previous paragraphs further characterized by:
the 1D array further comprises two sub arrays of ion chambers mounted back to back and orthogonal to the beam axis, in which:
(a) each collecting electrode comprises at least two conductive strips oriented in the direction of MLC pairs, lying on a plane surface;
(b) an ionization current collected by the conductive strips is measured by an electrometer connected electrically to the respective strip;
(c) at least two bias electrodes comprise a corresponding pair of conductive plates oriented in such a way that the distance between every strip and the bias electrode increases monotonically along the length of the strip;
(d) the two bias electrodes are substantially parallel; and
(e) at least one strip from each sub array is associated to a corresponding MLC leaf.

I. The device according to any of the paragraphs A-H, in which:
(a) an area below each corresponding leaf is shared by two collecting electrodes wherein the electrode comprises an individual thickness that changes monotonically when moving from one side of the leaf to the other; the thickness is measured in the plane of the electrodes. In the remainder of this specification, it will therefore be referred to as the width of the electrodes.
(b) an ionization current is collected by each electrode and the ionization current is measured by an independent electrometer electrically connected to the electrode; and
(c) a distance between the collecting electrodes and the bias electrodes is uniform throughout the array.

J. The device according to any of the paragraphs A-I, in which the 1D array is characterized by an array of ion chambers in which:
(a) collecting electrodes comprise a conductive strip oriented in the direction of MLC pairs, lying on a plane surface; the 'conductive' strip will be referred to in the remainder of this specification as 'resistive' strip.
(b) a bias electrode is a plate with uniform distance from the strip; and
(c) an ionization current collected by each strip is measured via two independent electrometers connected to the opposite extremities of the strip.

DETAILED DESCRIPTION OF THE INVENTION

This detailed description sets forth specific details of exemplary embodiments of the present invention to enable a thorough understanding: However, those of ordinary skill in the art understand that the scope of the present invention is not restricted to those embodiments. Other embodiments, whether described herein or omitted, may be practiced without these specific details. In other instances, well-known methods, procedures and components are not described in detail, thus avoiding obscuring the scope of the invention. Accordingly, this description does not limit the invention to the scope of the embodiments described. Although certain features are illustrated and described, many modifications, substitutions, changes, and equivalents will now occur to those of ordinary skill in the art. It is understood that the appended claims are intended to cover such modifications and changes as fall within the true spirit of the invention.

A beam model is a mathematical description of a radiation therapy apparatus in general and contains a number of parameters. These parameters take into account the characteristics of the accelerator (e.g., energy spectrum and lateral beam quality variations), the shapes and positions of the effective radiation sources, and the geometry and material of the beam shaping devices. A fluence is the number of photons/particles passing through a plane perpendicular to the beam per unit time and unit area. A fluence computation algorithm is a set of mathematical rules that computes the fluence according to the beam model and a given parameter set. The representation of the computed fluence (units, coordinate systems) is such that it is compatible with additional computational procedures for computing deposited dose in tissue and/or detector response. Useful descriptions of basic beam modelling techniques are provided, for example, by Wolfgang A. Tome, "*Beam Modelling for a Convolution/Superposition-Based Treatment Planning System*", Medical Dosimetry, Vol. 27, No. 1, pp. 11-19, 2002; or by Nikos Papanikolaou, "*Investigation of the convolution method for polyenergetic spectra*", Med. Phys. 20(5), 1993.

Figure 6:
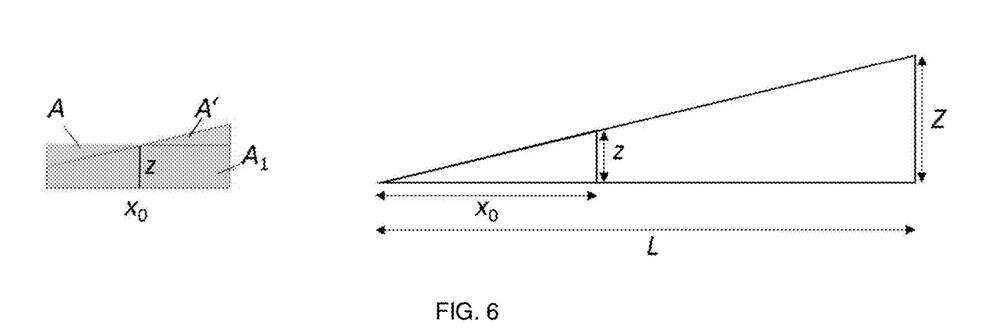
FIG. 6 illustrates a number of geometrical considerations made in relation to a detector according to the second embodiment.
Figure 7:
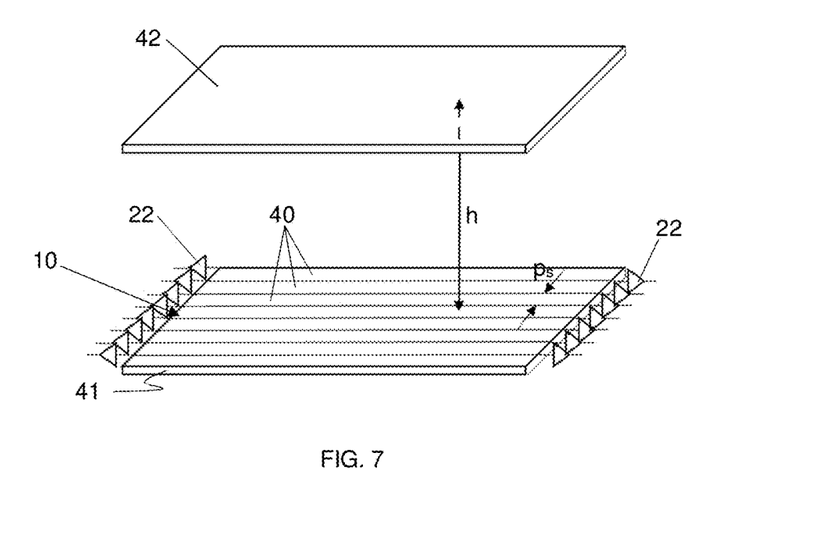
FIG. 7 is a 3D view of the main components of a detector in accordance with a third embodiment of the invention.
Figure 8:
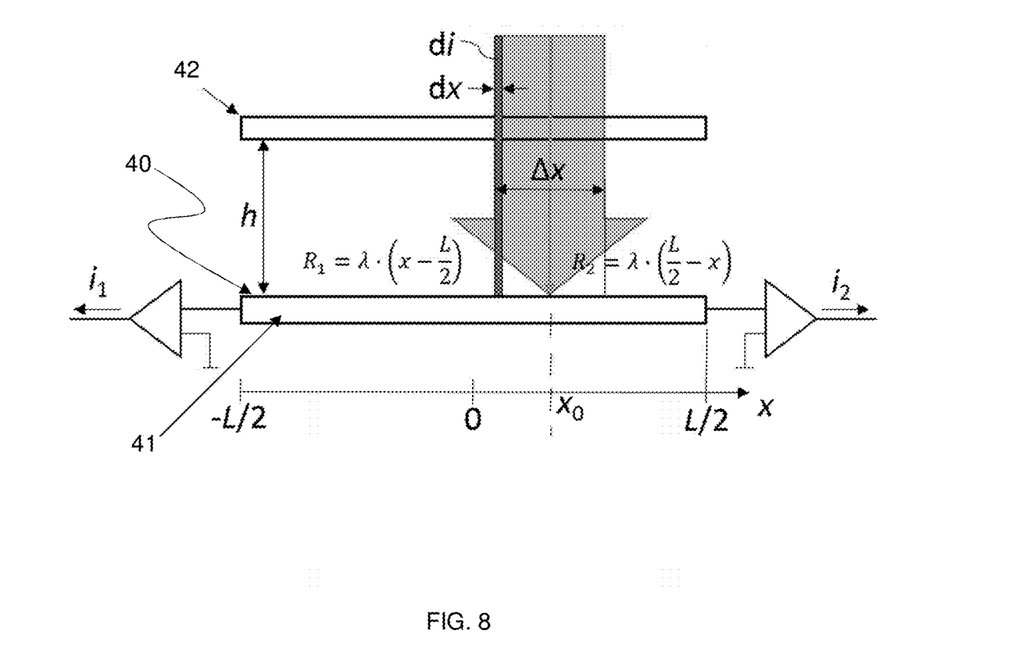
FIG. 8 is a side view of one collecting electrode strip of the detector according to the third embodiment, including a number of geometrical parameters needed to calculate the position of two leaves of the MLC.
Figure 9:
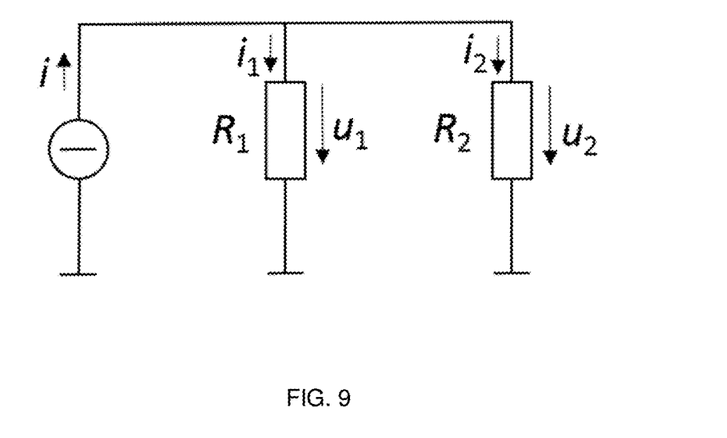
FIG. 9 illustrates the electrical equivalent of one collecting electrode strip in a detector according to the third embodiment.

Three technical solutions for the sensor have been identified, which allow the measurement of the aperture of each leaf pair AND the center of gravity of the aperture (it is not simply the measurement of a linear dose integral). These solutions are:

a) A double array of regular strips with inclined electrodes (FIG. 1-3)
b) Strips with variable width (FIG. 4-6)
c) Resistive strips (FIG. 7-9).

Barthelmes et al. (U.S. Pat. No. 4,803,368 issued 1989 Feb. 7) generally describes an ion chamber having inclined electrodes. Further, Islam et al. (U.S. Pat. No. 8,119,978 issued on 2012 Feb. 21) describes the use of strips with variable width in a single ion chamber. However, the present invention extends the teaching of the prior art. For example, the present invention includes for every leaf pair of an MLC, at least one ion chamber and two readout channels.

The sensing device according to the present invention comprises a detector that is built on the basis of a one-dimensional (1D) array of elongate ion chambers. The detector is configured to be attached to the head of a particle accelerator, usually a linear accelerator (LINAC). The accelerator head is equipped with a multi-leaf collimator and coupled to a rotatable gantry. Therefore, the detector rotates integrally to (meaning together with) the MLC, i.e. the detector is stationary relative to the rotating MLC, which itself can rotate together with the gantry or about the beam axis. There is a direct mapping between the ion chambers and the leaf-pairs of the MLC. This means that the number of ion chambers is chosen in accordance with the number of leaf pairs of the MLC. The ion chambers are defined by elongate conductive strips on a planar surface, preferably on a PCB, said strips acting as the collector electrodes of the ion chambers, and by a single bias electrode facing the strips, if the strips are present on one side of the planar surface, and by two bias electrodes, if the strips are present on both sides. According to a first and second embodiment, the strips are arranged in strip assemblies, each strip assembly comprising two strips, yielding two respective output currents. An integer number of strip assemblies is associated with each leaf pair when the detector is attached to the accelerator head. 'Associated with' means that a strip assembly is positioned to receive radiation passing through a particular leaf pair. For instance, the motion of a collimator's two banks of leaves, with 80 leaf-pairs may be tracked with a detector having 80 collector electrode strip assemblies, each strip assembly yielding two output currents. The strips connect to 160 corresponding channels of readout electronics. In contrast to conventional 2D arrays presently commercialized as online dosimeters, the present invention's number of 160 channels is remarkably lower than the number of pixels (from 1600 to 4000) of these 2D detectors.

According to a third embodiment, the strips are arranged as an array of single elongate strips, each strip yielding two output currents at its opposite outer ends. In the third embodiment therefore, an integer number of strips is associated with each leaf pair when the detector is attached to the accelerator head.

Ion chamber technology offers high reliability and performance with moderate manufacturing costs. The embodiments of the present invention may use, or be based upon, collecting electrodes manufactured using standard printed circuit board technology (PCB), which is widely available and economical.

Figure 1:
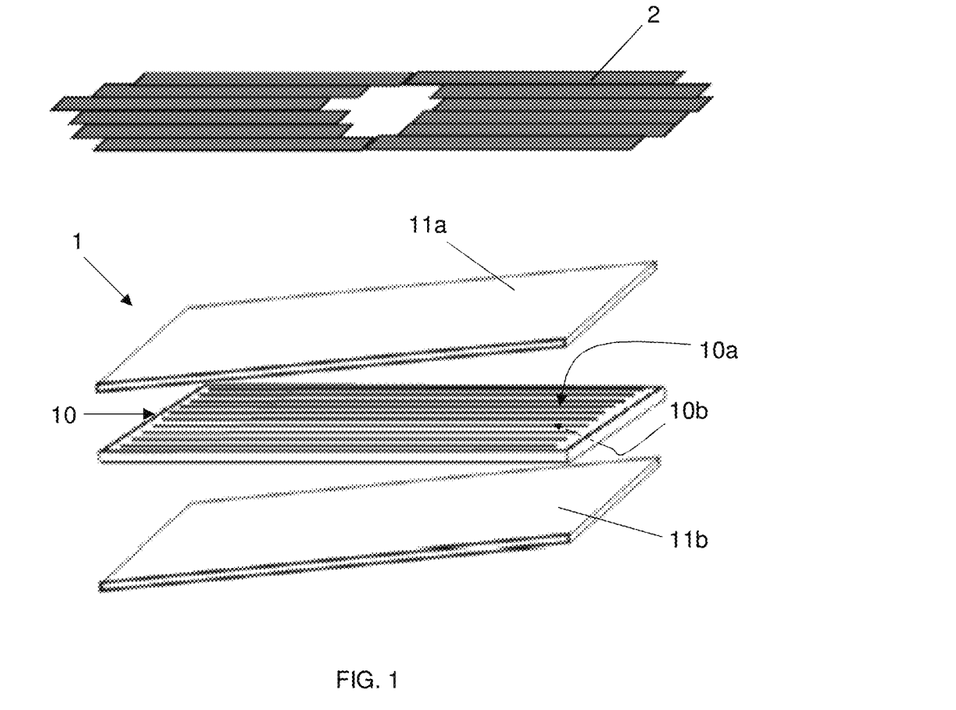
FIG. 1 is a 3D view of the main components of a detector in accordance with a first embodiment of the invention, and its position relative to a multi-leaf collimator (MLC).
Figure 2:
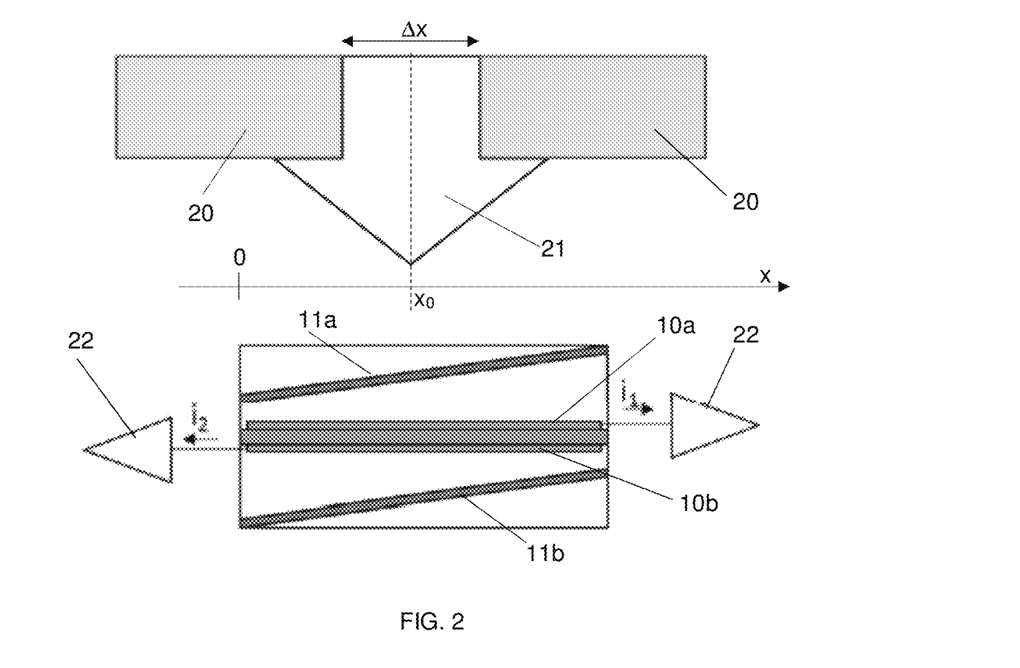
FIG. 2 is a side view of the detector in accordance with the first embodiment.
Figure 3:
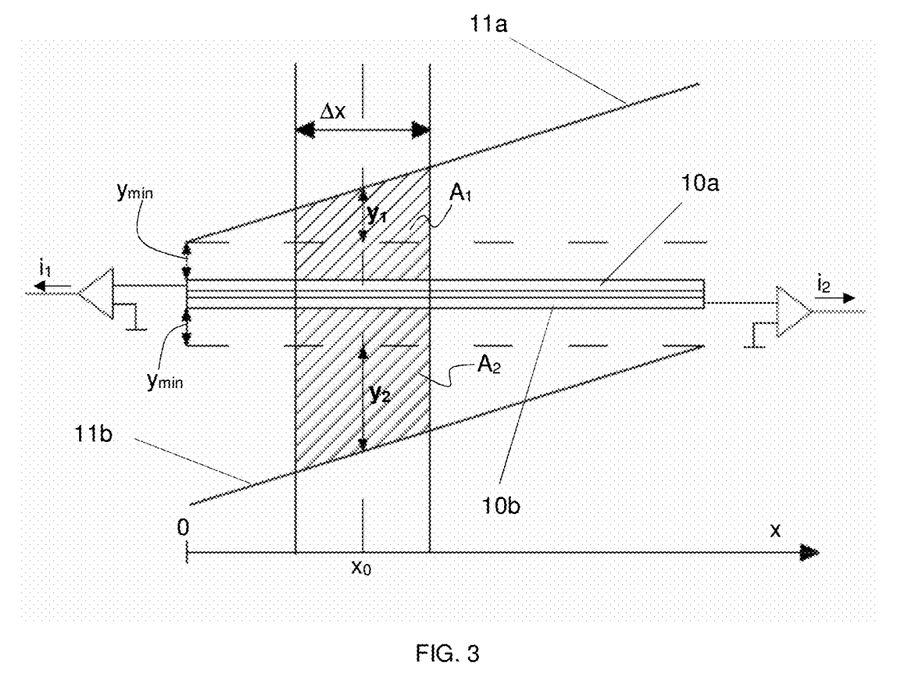
FIG. 3 is another side view of the collimator in accordance with the first embodiment, including indications of the geometrical parameters needed to determine the position of two leaves of the MLC.

FIGS. 1 to 3 illustrate a first embodiment of the present invention. FIG. 1 shows a 3D view of the main components of a detector 1 according to the first embodiment, as it is positioned relative to a MLC 2. The first embodiment configures, or is adapted, to measure the position of MLC leaves with a 1D array 10 of collector electrode strip assemblies. The detector comprises, or consists of, two sub-arrays 10a and 10b, which mount back to back. In each sub array, segmented collecting electrodes, in the form of printed PCB strips are combined with bias electrodes 11a and 11b in the form of simple, conductive planes placed at non-zero inclination angle relative to the strips. A 'strip assembly' in this embodiment is thus an assembly of two strips mounted back to back. All the strip assemblies are oriented in the direction of the collimator's leaf-movement. The drawing in FIG. 1 is a mere sketch, and does not clearly show the number of collector electrode strip assemblies in the 1D array. This number is preferably equal to the number of leaf pairs of the MLC 2, or it may be an integer multiple thereof. The embodiments described hereafter in more detail are based on the case wherein the number of strip assemblies is equal to the number of leaf pairs, and wherein the width of the strips is configured so that when the detector is attached to the accelerator head, each strip assembly in the array is associated with one corresponding leaf pair in the array of leaf pairs of the MLC (i.e. each strip assembly receives the radiation from one leaf pair). FIG. 2 illustrates in a side view the position of two leaves 20 of a leaf pair, relative to the detector 1. A collimated beam 21 passes through the opening defined by the leaves 20 and generates two currents $i_1$ and $i_2$ respectively, in the strips of the strip assembly that faces the leaf pair (i.e. that is positioned to receive the irradiation passing through said leaf pair). The first current $i_1$ is generated in the upper IC, between the bias electrode 11a and the upper collector electrode 10a. The second current $i_2$ is generated in the lower IC, between the bias electrode 11b and the lower electrode 10b. The detector comprises electrometers known as such in the art, which comprise at least a pair of amplifiers 22, for reading out the currents $i_1$ and $i_2$. According to a preferred embodiment, the bias electrodes 11a, 11b are mutually parallel.

Assuming that scattering and lateral spread of secondary electrons in the chamber volume can be neglected, the current collected by one side of the $n^{th}$ strip is given by the following proportionality relation (the symbol ∝ meaning 'proportional to'):

$$i_n \propto \int \Phi(x, y_n) k(x) \Delta y dx \quad (1)$$

Where Φ is the beam photon fluence, k(x) is the distance between the strip and the corresponding bias electrode, Δy is the strip width and $y_n$ is the position of the strip center along the array. For the detectors described hereafter, the above equation can be written in a simplified way.

The aim of each IC measurement is the determination of a dose D, applied in the IC volume by the incident radiation. "Dose" is the energy deposited by radiation in an amount of mass of material:

$$D = \frac{E}{m} = \frac{E}{V \cdot \rho} \quad (2)$$

where D=dose in Gy (1Gy=1 J/kg)
E=energy
m=mass
V=volume in m³ or mm³
ρ=density in kg/m³

What is measured however, is the charge Q produced in the sensitive volume.

$$Q = \frac{E}{W_{air}} \cdot e = \frac{D \cdot V \cdot \rho \cdot e}{W_{air}} \quad (3)$$

where $W_{air}$ is the ionization constant for air (the energy which is required to produce one pair of charges in air). The measured current i is the time derivative of the charge Q collected:

$$i = \frac{\dot{D} \cdot V \cdot \rho \cdot e}{W_{air}} = K \cdot V \text{ with } K = \frac{\dot{D} \cdot \rho \cdot e}{W_{air}} \quad (4)$$

where $\dot{D}$ is the dose rate (in Gy/min or Gy/s). $\dot{D}$ depends on the treatment machine emitting the ionizing radiation and its calibration. Air density is approximated with 1.2 kg/m³. $W_{air}$ and e are physical constants with the values $W_{air}$=33.97 eV respectively e=1.602·10⁻¹⁹ C. Here and in the following formulae, the proportionality constant K is calculated based on the system architecture or, alternatively, experimentally determined with a calibration procedure.

With the assumption that the fluence is uniform within the collimator aperture, the aperture Δx of a leaf pair and its center of gravity $x_0$, are determined from the currents $i_1$ and $i_2$ by the following proportionality relationships $$\Delta X \propto (i_1 + i_2)$$

$$x_0 \propto (i_1 - i_2)/(i_1 + i_2)$$

With reference to FIG. 3, the above relationships can be derived for the detector according to the first embodiment:

$$i_1 = K \cdot V_1 = K \cdot p_s \cdot \Delta x \cdot (y_{min} + \sin(\alpha) \cdot x_0) \quad (5)$$

$$i_2 = K \cdot V_2 = K \cdot p_s \cdot \Delta x \cdot (y_{min} + \sin(\alpha) \cdot (L - x_0)) \quad (6)$$

Herein, $p_s$ is the pitch of the array of collector electrodes (i.e. the pitch of each sub-array). This is a constant value for a given detector geometry. $p_s$ is equal to the strip width Δy plus the distance between two adjacent strips.

Δx and $x_0$ can be obtained from building the sum $i_1+i_2$ and the difference $i_1-i_2$ and result in:

$$\Delta x = \frac{i_1 + i_2}{K \cdot p_s \cdot (2y_{min} + \sin(\alpha) \cdot L)} = \frac{i_1 + i_2}{K'} \quad (7)$$

$$x_0 = \frac{L}{2} + \frac{i_1 - i_2}{2K \cdot p_s \cdot \Delta x \cdot \sin(\alpha)} \quad (8)$$

Additionally, the radiation flux is proportional to the sum of the current in all the strips. Knowing the position of the leaves and flux enables one to prove delivery of the prescribed plan (expressed, e.g., in terms of MU/sampling interval, MU/segment or MU/control point), wherein 'MU' stands for 'Monitor Units'.

Those having ordinary skill in the art will appreciate that other solutions, alternative to the above-described inclined electrode ion chambers, can easily be figured out, leading to similar relationship between leave positions and measured current. The key point is that the sensitivity of each strip has to be modulated along its length to give sensitivity to beam position $x_0$.

Figure 4:
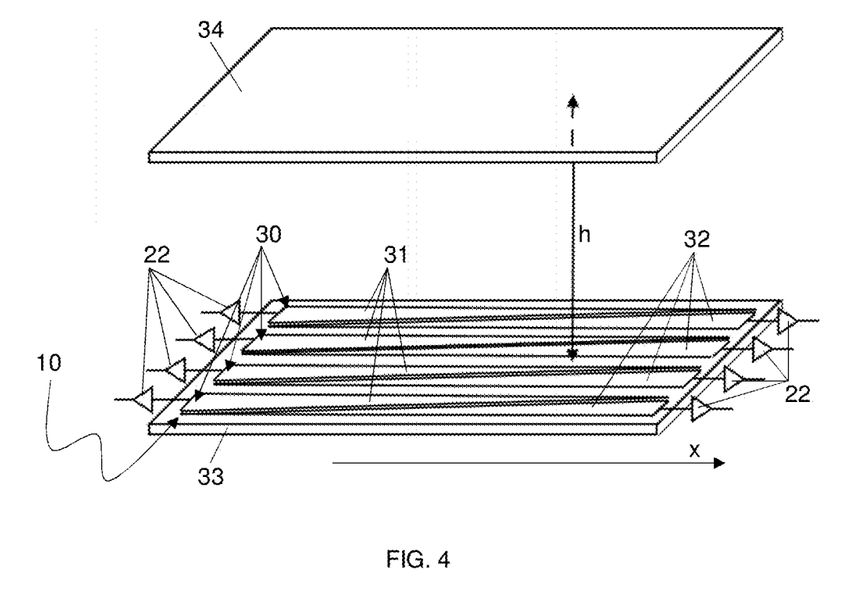
FIG. 4 is a 3D view of the main components of a detector in accordance with a second embodiment of the invention.
Figure 5:
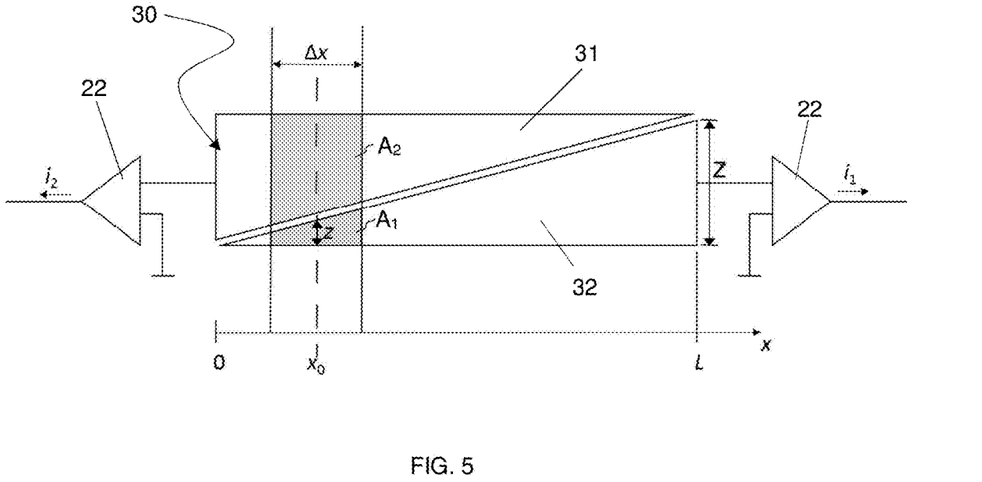
FIG. 5 is a plane view of one collecting electrode strip in a detector according to the second embodiment.

A second embodiment of the present invention includes the 1D array 10 of collector electrode strips shown in FIGS. 4-6. Here each strip assembly 30 consists of a set of adjacent electrodes 31 and 32 printed on the same side of a PCB 33. single bias electrode 34 is provided. The bias electrode 34 is a conductive surface parallel to the collecting electrodes, i.e. at a constant distance h from the array of collecting electrode strips 30. The width of the collecting electrodes 31 and 32 changes monotonically in the x-direction but at an opposite rate. In other words, the first electrode 31 decreases monotonically from high width to low width in the direction +x, while the second electrode 32 increases monotonically from low width to high width in the same direction +x. According to the preferred embodiment, for a given position x, the sum of the width of both strips at this position is constant. The width of the electrodes thereby modulates sensitivity along the length. The detector is again positioned relative to an MLC (not shown) so that an integer number of strip assemblies 30 is associated with each leaf pair. In detail, when each strip assembly 30 is associated with only one leaf pair, the area below the leaf-pair is shared by two collecting electrodes 31 and 32, which are read-out by independent electrometers (comprising at least two amplifiers 22 coupled respectively to the first and second electrodes 31 and 32), and which produce $i_1$ and $i_2$ for each IC strip 30. The geometry for a single collecting electrode strip is shown in detail in FIG. 5, from which the formulas for Δx and $x_0$ can be derived.

In case of the triangular strips design shown in FIG. 5, the active area of the IC varies while the height h is constant (see FIG. 4). Therefore, the current i in the IC is proportional to the area A. The areas $A_1$ and $A_2$ (see FIG. 5) can be expressed using geometric parameters of the strip as well as the parameters Δx and $x_0$ as follows:

$$i_1 = K \cdot A_1 = K \cdot \Delta x \cdot z = K \cdot \Delta x \cdot \frac{z}{L} \cdot x_0 \quad (9)$$

$$i_2 = K \cdot A_2 = K \cdot \Delta x \cdot (Z - z) = K \cdot \Delta x \cdot Z\left(1 - \frac{x_0}{L}\right) \quad (10)$$

To obtain these equations, some geometric considerations shown in FIG. 6 were made. On the left hand side, it is illustrated that the respective area $A_i$ can be calculated like a square area, since A=A'. Additionally, the following relationship between z, Z, L, and $x_0$ (illustrated on the right hand side) is applied:

$$\frac{Z}{L} = \frac{z}{x_0} \leftrightarrow Z = \frac{Z}{L} \cdot x_0. \tag{11}$$

From the two currents $i_1$ and $i_2$, $\Delta x$ and $x_0$ can be determined as follows $$\Delta x = \frac{i_1 + i_2}{K \cdot Z} \tag{12}$$

$$x_0 = \frac{L}{2} \cdot \frac{i_1 - i_2}{i_1 + i_2} \tag{13}$$

FIGS. 7 to 9 illustrate the third embodiment of the present invention. Here, each strip 40 of the array 10 is a single collecting electrode on a common PCB 41. The strips are adjacent and isolated from each other, and arranged at a pitch $p_s$. A single bias electrode 42 is placed at a constant height h above the strips 40 (i.e. parallel to the strip array). The strips 40 are read-out at both ends by separate electrometers comprising at least amplifiers 22. This solution works as long as the resistivity of the strip is high enough to limit the parasitic current generated by the voltage offset of the readout amplifiers, and/or to obtain signals with a sufficiently high signal to noise ratio 22. FIG. 8 shows the geometry of one strip 40 relative to the bias electrode 42. The resistance R of the strip 40 depends on the length L (or rather x in the general case as indicated in FIG. 8 for the length coordinate) and resistance per unit length $\lambda$ of the resistive material:

$$\lambda = \frac{R}{L} \text{ and } R = L \cdot \lambda \tag{14}$$

When a pencil beam creates free charges in the region above the resistive strip at location x, these currents are collected on the strip and flow towards the electrometer amplifiers through resistors $R_1$ and $R_2$ formed by the resistive material. The current causes a voltage drop over those resistors on both sides of the intersection of the pencil beam with the strip. As the inputs to the electrometer amplifiers are at ground potential, this can be described as a parallel circuit with two branches in which a division of currents into partial currents $i_1$ and $i_2$ takes place. This principle is visualized in FIG. 9. The sum of $i_1$ and $i_2$ always equals the total current.

For the circuit as sketched in FIG. 9, the following general equations can be defined:

$$i = i_1 + i_2 \tag{15}$$

$$u_1 = u_2 \text{ or } R_1 \cdot i_1 = R_2 \cdot i_2 \tag{16}$$

$$\text{with } R_1 = \lambda \cdot \left(x - \frac{L}{2}\right) \text{ and } R_2 = \lambda \cdot \left(\frac{L}{2} - x\right) \tag{17}$$

In order to obtain $i_1$ and $i_2$, Equation 15, 16 and 17 can be transformed:
By applying $i_1 = i - i_2$ resp. $i_2 = i - i_1$
and $R = R_1 + R_2$ (total resistance=constant)

the currents $i_1$ and $i_2$ can be described as:

$$i_1 = i \cdot \frac{R_2}{R} \text{ and } i_2 = i \cdot \frac{R_1}{R}. \tag{18}$$

As explained above, the current in an IC is proportional to the volume or area of the chamber (depending on the IC design). Therefore, the derivative must be proportional to the derivative of the volume or area, too:

$$di = K \cdot dA$$

where K is a constant containing the sensitivity of the chamber and A is the area of the collecting electrode. In case of the resistive strip design, two dimensions of the chamber volume remain constant: the strip pitch $p_s$ as well as the chamber height h (distance between the strip array and the bias electrode, see FIG. 8). Therefore, only one dimension of the volume V varies, namely, its length, x. di can be determined as $$di = K \cdot dx. \tag{19}$$

The broad beam may be described as the sum of an (infinite) number of pencil beams, each of width dx. The current di (comprised of $di_1$ and $di_2$) is created by the charges formed in the area which is hit by the pencil beam of width dx. Therefore, applying Equations 18 and 19, the currents $di_1$ resp. $di_2$ induced in the strip can be written as $$di_1 = \frac{R_2}{R} \cdot di \text{ and } di_2 = \frac{R_1}{R} \cdot di.$$

With use of Equation 17, it can be concluded that $$di_1 = \frac{R_2}{R} di = \frac{\lambda \cdot \left(\frac{L}{2} - x\right)}{R} \cdot K \, dx$$

and analogously $$di_2 = \frac{R_1}{R} di = \frac{\lambda \cdot \left(x - \frac{L}{2}\right)}{R} \cdot K \, dx.$$

The currents $i_1$ and $i_2$ created by a broad beam, are obtained as the continuous sum of all the partial currents $di_1$ respectively $di_2$. Exemplarily, calculations for $i_1$ are presented here; calculations for $i_2$ were performed analogously.

$$i_1 = \int_{x_0 - \frac{\Delta x}{2}}^{x_0 + \frac{\Delta x}{2}} \frac{\lambda \cdot \left(\frac{L}{2} - x\right)}{R} \cdot K \, dx = \frac{\lambda K}{2R}\left(\frac{L}{2} - x\right)^2 \bigg|_{x_0 - \frac{\Delta x}{2}}^{x_0 + \frac{\Delta x}{2}} = \frac{\lambda K}{2R}\left[\left(\frac{L}{2} - x_0 + \frac{\Delta x}{2}\right)^2 - \left(\frac{L}{2} - x_0 - \frac{\Delta x}{2}\right)^2\right]$$

$$= \frac{\lambda K}{2R} \cdot 2\Delta x \left(\frac{L}{2} - x_0\right) = \frac{K}{L}\Delta x\left(\frac{L}{2} - x_0\right)$$

After integration, $i_1$ and $i_2$ can be written as:

$$i_1 = \frac{K}{L}\Delta x\left(\frac{L}{2} - x_0\right) \text{ and} \tag{20}$$

$$i_2 = \frac{K}{L}\Delta x\left(\frac{L}{2} + x_0\right) \tag{21}$$

From these two equations $\Delta x$ and $x_0$ can be determined:

$$\Delta x = \frac{i_1 + i_2}{K} \tag{22}$$

$$x_0 = \frac{L}{2}\frac{i_1 - i_2}{i_1 + i_2} \tag{23}$$

In any of the embodiments described above, as in any ionization chamber measurement, a measurement is required of the dose rate $\dot{D}$ in order to calculate the value of K (see equation (4)). The dose rate is typically obtained from ionization chamber detectors included in the standard equipment of most irradiation accelerator types. In a LINAC the dose rate is usually measured by a redundant system in the form of two independent ionization chambers. When the sensing device of the invention is mounted on such a LINAC, the dose rate measurement obtained from this redundant system may be used to determine K. The integration over time of $\dot{D}$ yields the dose D.

In special forms of the second and third embodiment, a large area ionization chamber may be added on the back side of the array of strips. The large area chamber may be realized by providing a large collecting electrode on the backside of the PCB carrying the strip assemblies 30 (in the case of the second embodiment), or the strips 40 (in the case of the third embodiment). The surface of the large collecting electrode is large enough to receive a beam shaped by any configuration of the MLC. The surface preferably covers an area corresponding to the combined area of the strip assemblies 30 or of the strips 40. A second bias electrode is then provided, on the opposite side of the first bias electrode 34 or 42, preferably at the same distance h from the large collecting electrode, but this distance may also be different from h. An electrometer is further provided for measuring a current output from the large area collector electrode when an electric field is created between the large area collector electrode and the second bias electrode, and when a beam passes through the large area chamber. The large area ionization chamber thus created on the backside of the strips allows to obtain a measurement of the dose rate $\dot{D}$.

A sensing device according to the invention comprises a detector equipped with an array of ion chambers according to any of the above-described embodiments or equivalents thereof. In addition, the sensing device comprises a processor configured to determine the position of at least one pair of leaves of the MLC using the currents $i_1$ and $i_2$ obtained from the collecting electrode strips. In other words, the processor is configured to calculate $\Delta x$ and $x_0$ on the basis of predefined formulae which depend on the treatment setup and the detector type, as described above for three particular embodiments. This functionality of the processor is clear as such. The design and practical implementation of the processor may be executed according to known technology. The sensing device further comprises a gantry sensor configured to determine at least one position associated with a first gantry angle. In other words, the gantry sensor detects the angular position of the gantry, allowing the determined detected parameters of the MLC leaves ($\Delta x$ and $x_0$) to be compared to prescribed parameters included in a treatment program for specific gantry angles. An angle sensor is known as such and therefore not described in detail.

The procedures outlined above represent a first approximation to obtain the position of the leaves from measured current. This approach is acceptable if scattering and lateral spread of electrons are negligible. If this is not the case, a more refined calculation, using the signal from neighbor strips, is performed. In this case $\Delta x$ and $x_0$ are calculated using the signal from neighbor strips too.

Leaf aperture and flux are not sufficient alone to determine fluence $\Phi(x,y)$. If, however, this data is supplemented by independent measurements, e.g. beam profiles measured during LINAC commissioning or periodic QA, then $\Phi(x,y)$ can be determined. Fluence data is fed into a dose engine in conjunction with patient images (e.g. CT scan) to determine the actual dose delivered in the patient's anatomy. Lastly, this dose distribution is compared to the planned one.

Many LINACs provide a listing of operational parameters during or after the delivery of a treatment (often called log files). These parameters include the evolution of the collimator configuration, the number of delivered MU and the gantry angle. In principle, these parameters should match the requirements of the plan, although deviations are possible due to malfunctioning, or constraints of real operation that were not accounted in the TPS. The machine determines these parameters with a high resolution (e.g. 0.1 mm in leaf position), probably higher than what is achievable by the proposed 1D system: However, log files are not always suitable for QA purposes because the device under exam also generates the data, and a redundant QA process is not possible.

One additional contemplated use of the present invention's proposed system is to verify that measurements are consistent with log files (within experimental uncertainty), and to use the log files to determine the fluence and the dose into the patient.

The invention claimed is:

1. A sensing device for a radiation therapy apparatus, the apparatus comprising an accelerator, a beam-shaping device, the beam shaping device being a multi-leaf collimator (MLC) having a plurality of pairs of leaves, and a rotatable gantry, the sensing device comprising:

a transmission electronic detector comprising one or two bias electrodes and a planar 1D array of electrically conductive strip assemblies, and wherein:

each strip assembly comprises two strips which are oriented in the direction of the leaf pairs, and configured so that each leaf pair of the MLC is associated with one or more strip assemblies, when the detector is positioned between the MLC and a target of interest, each strip together with one of the bias electrodes defines an ion chamber, with the strip forming the collecting electrode thereof, the two strips of each assembly are configured to respectively produce two currents $i_1$ and $i_2$ when the detector is irradiated by a beam that is shaped by the MLC, and when an electric field is created between the bias electrode(s) and the strips, said currents are used to determine the position of the pair of MLC leaves associated with the strip assembly, for each strip assembly, a pair of electrometers comprising respective read-out amplifiers coupled respectively to the strips of the assembly, for measuring the currents $i_1$ and $i_2$, a gantry sensor configured to determine at least one position associated with a gantry angle; and a processor, adapted to determine the position of at least one pair of leaves of the MLC using the currents $i_1$ and $i_2$ obtained from the strip assemblies.

2. The sensing device according to claim 1, wherein each strip assembly comprises two collecting electrodes mounted back to back, and wherein the detector comprises two planar bias electrodes which are conductive plates placed on either side of the planar 1D array of strip assemblies, and oriented in such a way that the distance between every strip on one side of the planar 1D array and the corresponding bias electrode increases monotonically along the length of the strip in a given direction along said length, while the distance between every strip on the other side and the corresponding bias electrode decreases monotonically along the length of the strip, in the same given direction.

3. The sensing device according to claim 2, wherein the bias electrodes are parallel to each other.

4. The sensing device according to claim 1, wherein each strip assembly comprises two adjacent collecting electrode strips, and wherein the width of the first electrode strip decreases monotonically along the length of the strip assembly in a given direction along said length, while the width of the second electrode strip increases monotonically in the same given direction, and wherein the detector further comprises one bias electrode in the form of a conductive plate that is parallel to the planar array of strip assemblies.

5. The sensing device according to claim 4, further comprising a large area collecting electrode on the back side of the planar array of strip assemblies, and a second bias electrode parallel to the planar array of strip assemblies and facing said large area collecting electrode.

6. A sensing device for a radiation therapy apparatus, the apparatus comprising an accelerator, a beam-shaping device, the beam shaping device being a multi-leaf collimator (MLC) having a plurality of pairs of leaves, and a rotatable gantry, the sensing device comprising:

a transmission electronic detector comprising a bias electrode and a planar 1D array of electrically conductive strips oriented parallel to the bias electrode, and wherein:

each strip is oriented in the direction of the leaf pairs, and configured so that each leaf pair of the MLC is associated with one or more strips, when the detector is positioned between the MLC and a target of interest, each strip together with one of the bias electrodes defines an ion chamber, with the strip forming the collecting electrode thereof, each strip is configured to respectively produce two currents $i_1$ and $i_2$ at the opposite outer ends of the strip, when the detector is irradiated by a beam that is shaped by the MLC, and when an electric field is created between the bias electrode(s) and the strips, said currents are used to determine the position of the pair of MLC leaves associated with the strip assembly, for each strip, a pair of electrometers comprising respective read-out amplifiers coupled respectively to the opposite outer ends of the strip, for measuring the currents $i_1$ and $i_2$, a gantry sensor configured to determine at least one position associated with a gantry angle; and a processor, adapted to determine the position of at least one pair of leaves of the MLC using the currents $i_1$ and $i_2$ obtained from the strips.

7. The sensing device according to claim 6, further comprising a large area collecting electrode on the back side of the planar array of strips, and a second bias electrode parallel to the planar array of strips and facing said large area collecting electrode.

8. The sensing device according to claim 1 wherein the sensing device further comprises a receiver, configured to receive a patient plan (including patient dose, patient images taken before planning and radiation beam configuration); and the processor is adapted to compare expected (from plan) and measured LINAC behavior (in term of leaves position, flux and gantry angle).

9. The sensing device of claim 8 wherein the processor is further configured to enable real-time signalling of a deviation from an expected behavior and a measured behavior exceeding a user-defined tolerance.

10. The sensing device of claim 8, further comprising:

a storage means in communication with the processor, the storage means configured to store a beam model of the accelerator;

a fluence-reconstructing engine configured to compute a photon fluence based on the position of pairs of the leaves determined by the processor and on the beam model wherein the photon fluence is determined independently from a presence of a patient or phantom in the beam; and a dose calculation engine configured to compute a delivered 3D dose distribution using fluence and patient images.

11. The sensing device of claim 9 wherein the processor is further adapted to compare a calculated delivered dose to a planned dose.

12. The sensing device of claim 9 wherein:

the processor is further configured to extract at least one subset of a 3D dose distribution and a set of quality parameters from the calculated 3D dose distribution.

13. The sensing device of claim 9 further comprising:

an image acquisition station configured to acquire updated patient images;

an image processor configured to communicate the images to the dose calculation engine whereby the dose calculation engine calculates a dose distribution based on measured fluence and the updated patient images.

14. The sensing device according to claim 9 wherein the processor is further adapted to accumulate a plurality of data measurements relating to a corresponding plurality of dose delivered to the patient during consecutive fractions.

15. The sensing device according to claim 12 wherein the processor is further adapted to accumulate a plurality of data measurements relating to a corresponding plurality of dose delivered to the patient during consecutive fractions.

* * * * *